US00PP31371P2

(12) United States Plant Patent
Hansen

(10) Patent No.: US PP31,371 P2
(45) Date of Patent: Jan. 14, 2020

(54) ***DELOSPERMA* PLANT NAMED 'TANGERINE TANGO'**

(50) Latin Name: ***Delosperma* hybrid**
Varietal Denomination: Tangerine Tango

(71) Applicant: Christopher M. Hansen, Zeeland, MI (US)

(72) Inventor: Christopher M. Hansen, Zeeland, MI (US)

( * ) Notice: Subject to any disclaimer, the term of this patent is extended or adjusted under 35 U.S.C. 154(b) by 0 days.

(21) Appl. No.: 16/350,510

(22) Filed: Nov. 26, 2018

(51) Int. Cl.
*A01H 5/02* (2018.01)
*A01H 6/00* (2018.01)

(52) U.S. Cl.
USPC ..... Plt./422
CPC ..... *A01H 6/00* (2018.05)

(58) Field of Classification Search
USPC ..... Plt./422
See application file for complete search history.

*Primary Examiner* — Anne Marie Grunberg
(74) *Attorney, Agent, or Firm* — Penny J. Aguirre

(57) ABSTRACT

A new cultivar of *Delosperma* plant named 'Tangerine Tango' that is characterized by its floriferous blooming habit, its red-orange flowers with white centers, its very compact and tight mounds of foliage that do not become long or leggy during the summer growing months, its strong re-blooming habit during the entire growing season and into late fall, its small plant size, its uniform rooting habit, and its uniform blooming period with other plants in the series.

2 Drawing Sheets

Botanical classification: *Delosperma* hybrid.
Variety denomination: 'Tangerine Tango'.

CROSS REFERENCE TO RELATED APPLICATIONS

This application is co-pending with U.S. Plant patent Applications filed for plants derived from the same breeding program that are entitled *Delosperma* Plant Named 'Coconut Crush' (U.S. Plant patent application Ser. No. 16/350,512), *Delosperma* Plant Named 'Fig Fusion' (U.S. Plant patent application Ser. No. 16/350,511), *Delosperma* Plant Named 'Pumpkin Perfection' (U.S. Plant patent application Ser. No. 16/350,509), *Delosperma* Plant Named 'Banana Blast' (U.S. Plant patent application Ser. No. 16/350,513), and *Delosperma* Plant Named 'Saucy Strawberry' (U.S. Plant patent application Ser. No. 16/350,514).

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

BACKGROUND OF THE INVENTION

The present invention relates to a new and distinct cultivar of *Delosperma* plant of hybrid origin, botanically known as *Delosperma* 'Tangerine Tango' and will be referred to hereinafter by its cultivar name, 'Tangerine Tango'. The new cultivar of *Delosperma* is a hardy herbaceous perennial grown for use as a landscape and container plant and is particularly suitable as a groundcover.

'Tangerine Tango' arose from an ongoing breeding program by the Inventor in Hudsonville, Mich. The objective was to obtain a new series of *Delosperma* cultivars with more floriferous blooming habits, smaller and more compact and uniform plant habits, and blooming periods that are the same amongst all cultivars in the series when grown under the same conditions.

The Inventor made a controlled cross in July of 2014 in his test garden in Hudsonville, Mich. between an unnamed proprietary plant from the Inventor's breeding program, reference no. 275-3, as the female parent and pollen that was pooled from unnamed proprietary plants of *Delosperma* as the male parent. The exact male parent is therefore unknown. The Inventor selected 'Tangerine Tango' as a single unique plant in June of 2016 from the resulting seedlings.

Asexual reproduction of the new cultivar was first accomplished by stem tip cuttings in April of 2015 in Hudsonville, Mich. Asexual propagation by stem tip cuttings has determined that the characteristics are stable and reproduced true to type in successive generations.

SUMMARY OF THE INVENTION

The following traits have been repeatedly observed and are determined to be the characteristics of the new cultivar. These attributes in combination distinguish 'Tangerine Tango' as a unique cultivar of *Delosperma*.

1. 'Tangerine Tango' exhibits a floriferous blooming habit with an average of 65 flowers per plant as a 10-week-old plant grown in a 1-quart container started from a 128-cell plug.
2. 'Tangerine Tango' exhibits red-orange flowers with white centers.
3. 'Tangerine Tango' exhibits very compound and tight mounds of foliage that do not become long or leggy during the summer growing months.

4. 'Tangerine Tango' exhibits a strong re-blooming habit during the entire growing season and into late fall.
5. 'Tangerine Tango' exhibits a height of 3.8 cm and 38 cm in width.
6. 'Tangerine Tango' exhibits uniform rooting that occurs in just 10 days.
7. 'Tangerine Tango' exhibits a uniform blooming period with other plants in the series.

The seed parent plant of 'Tangerine Tango', no. 275-3, differs from 'Tangerine Tango' in having a 30% less compact plant habit, 50% less flowers and flowers that lacked bright white centers. 'Tangerine Tango' can be most closely compared to the cultivars 'Jewel of Desert Ruby' (U.S. Plant Pat. No. 23,453) and 'WOWDOY3' (U.S. Plant Pat. No. 25,600). 'Jewel of Desert Ruby' is similar to 'Tangerine Tango' in having orange flowers with white centers and a flowering period of late spring through fall. 'Jewel of Desert Ruby' differs from 'Tangerine Tango' in having less flowers; 40 flowers per 10-week old plant, a taller plant height varying between 56 cm and 71 cm, and a less floriferous re-bloom in fall. 'WOWDOY3' is similar to 'Tangerine Tango' in having a similar blooming habit during the summer and succulent leaves that are green in color. 'WOWDOY3' differs from 'Tangerine Tango' in having larger flowers and less flowers; 35 flowers per 10-week old plant, and a less compact plant habit with a taller plant height of 10 cm, and wider plant width of 91 cm. 'Tangerine Tango' can also be compared to cultivars with co-pending patent applications from the same breeding program that have the same blooming periods. 'Coconut Crush' differs from 'Tangerine Tango' in having white flowers, 'Fig Fusion' differs from 'Tangerine Tango' in having hot pink flowers, 'Pumpkin Perfection' differs from 'Tangerine Tango' in having orange flowers, 'Saucy Strawberry' differs from 'Tangerine Tango' in having red-pink flowers, and 'Banana Blast' differs from 'Tangerine Tango' in having red-orange flowers.

BRIEF DESCRIPTION OF THE DRAWINGS

The following is a detailed description of the new cultivar as observed on 3-month-old plants of 'Tangerine Tango' as grown outdoors in two-quart containers in Hudsonville, Mich.

The photograph in FIG. 1 provides a view of 'Tangerine Tango' in bloom.

Figure 1:
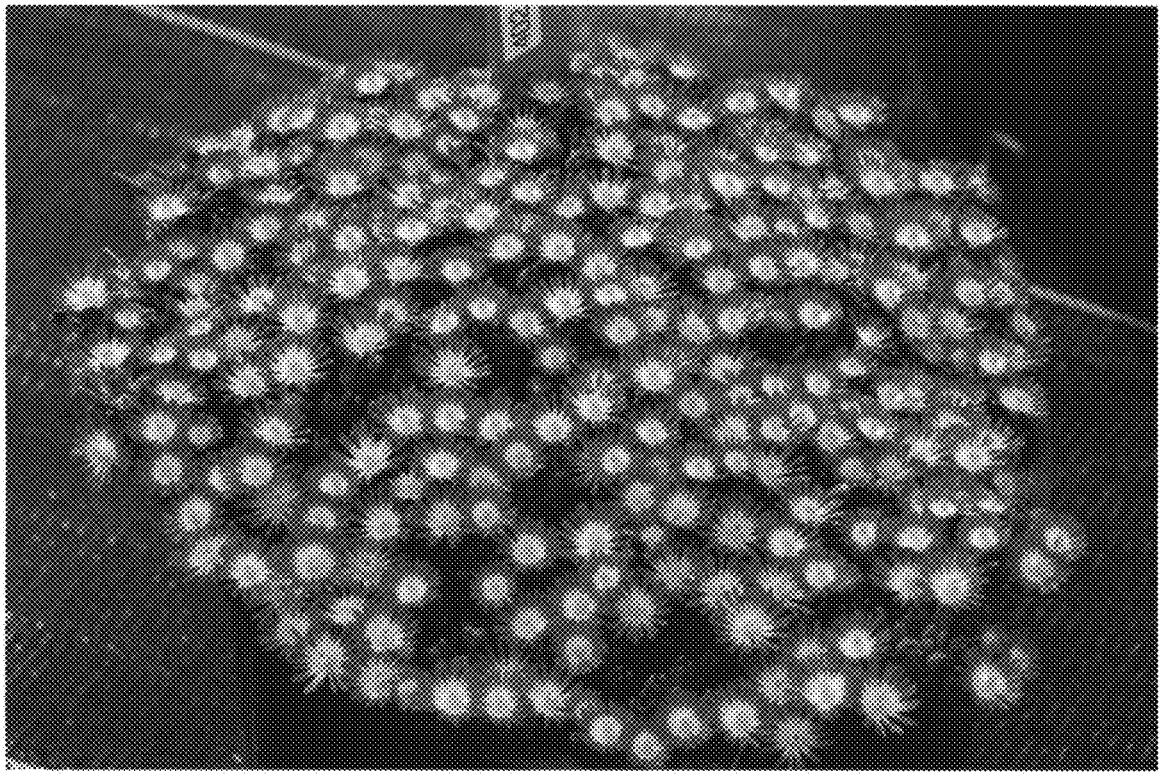
Figure 2:
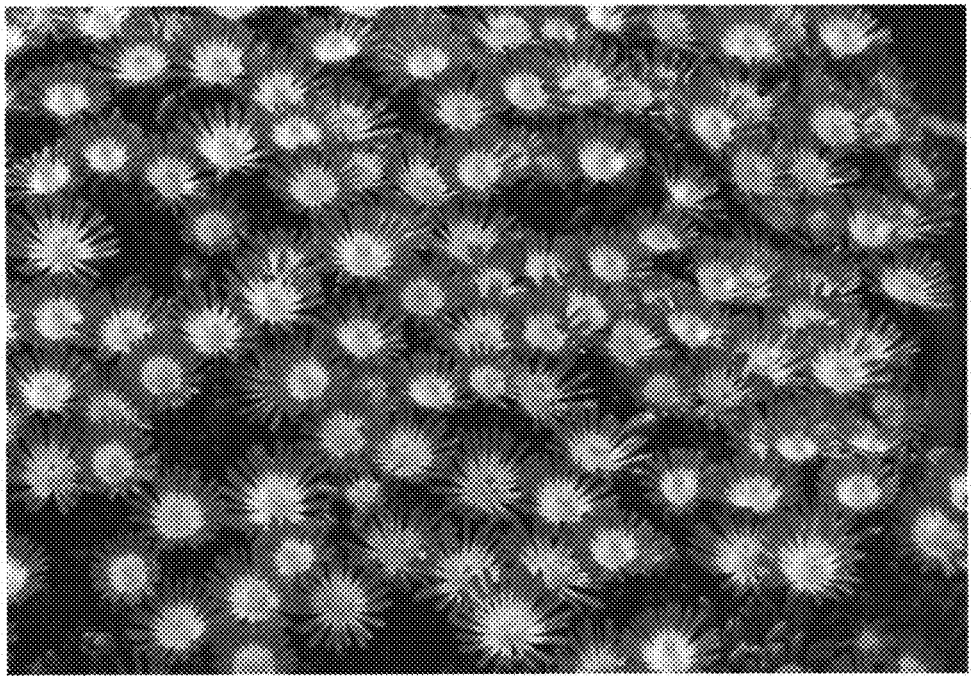

The photograph in FIG. 2 provides a close-up view of 'Tangerine Tango' in bloom.

Figure 3:
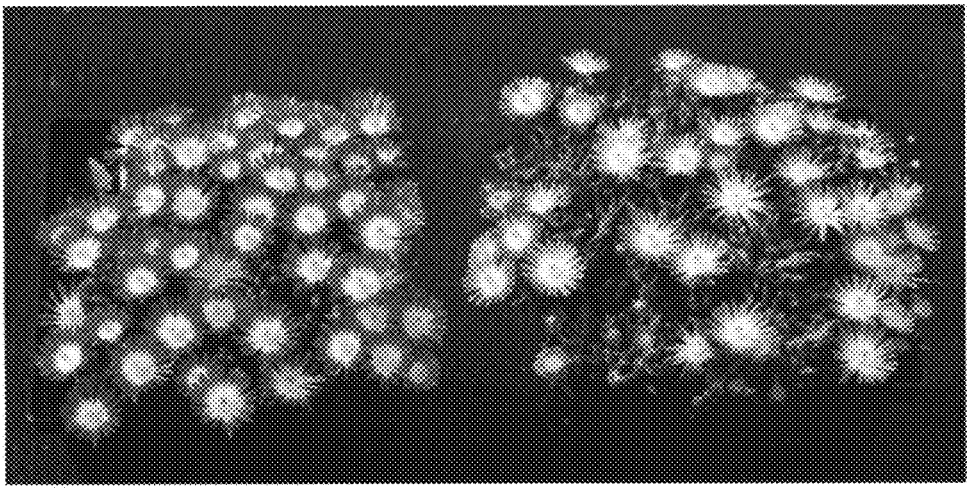

The photograph in FIG. 3 provides a comparison of 'Tangerine Tango' (left) and 'Jewel of Desert Ruby' (right).

The colors in the photograph may differ slightly from the color values cited in the detailed botanical description, which accurately describe the colors of the new *Delosperma*.

DETAILED BOTANICAL DESCRIPTION

The following is a detailed description of 3-month-old plants of the new cultivar as grown in 9-cm containers outdoors in Hudsonville, Mich. The phenotype of the new cultivar may vary with variations in environmental, climatic, and cultural conditions, as it has not been tested under all possible environmental conditions. The color determination is in accordance with The 2015 Colour Chart of the Royal Horticultural Society, London, England, except where general color terms of ordinary dictionary significance are used.

General description:

*Blooming period.*—Heavy bloom from June 1 through July, then re-blooming through late October.

*Plant type.*—Herbaceous perennial.

*Plant habit.*—Clumping, tightly mounded, compact ground cover.

*Height and spread.*—An average of 3.8 cm in height and about 38 cm in diameter in the landscape.

*Hardiness.*—At least in U.S.D.A. Zones 6 to 9.

*Diseases and pests.*—No susceptibility or resistance to diseases or pests has been observed.

*Root description.*—Fibrous roots, 199A in color.

*Root development.*—Cuttings root uniformly in 128-cell plugs in 6 weeks, 128-cell planted into a 9-cm pot or quart pot will finish and be in full bloom at 9 to 10 weeks after planting.

*Propagation.*—Stem tip cuttings.

*Growth habit.*—Moderate.

Stem description:

*Shape.*—Round.

*Stem color.*—Young stems; 138D, older stems 152A.

*Stem size.*—An average of 4 cm in length and 1 mm in diameter.

*Internode length.*—An average of 1 to 3 mm.

*Stem substance.*—Succulent, lower older stems become slightly woody.

*Stem surface.*—Young; moderately glossy and glabrous, mature is woody.

*Stem strength.*—Young; moderately strong, mature; strong.

*Branching habit.*—Freely and very densely branching, both basal and lateral, an average of 16 lateral branches per basal stem and 30 basal stems per plant.

Foliage description:

*Leaf shape.*—Ligulate, oblong and narrow.

*Leaf substance.*—Succulent, thick.

*Leaf division.*—Simple.

*Leaf base.*—Cuneate.

*Leaf apex.*—Acute.

*Leaf venation.*—None visible.

*Leaf margins.*—Entire.

*Leaf arrangement.*—Opposite to whorled.

*Leaf surface* (*upper and lower surface*).—Densely pubescent with very short glandular hairs; too small to measure.

*Leaf color.*—Young and mature leaves; base 138D blending upward and becoming 138A.

*Leaf size.*—About 3 cm in length and 3 mm in width.

*Leaf quantity.*—Average of 5 per lateral branch.

*Leaf attachment.*—Sessile.

Inflorescence description:

*Inflorescence type.*—Flowers solitary, terminal.

*Flower number.*—Densely floriferous, an average of 12 per lateral stem.

*Flower fragrance.*—None.

*Flower aspect.*—Mostly held upright.

*Flower longevity.*—A few days, self-cleaning.

*Flower type.*—Single.

*Flower size.*—Average of 1.5 cm in diameter and 9 mm in depth.

*Flower buds.*—Broadly ovate to oblong in shape, an average of 1 cm in depth and 6 mm in diameter, color; 143A, surface is densely pubescent with minute hairs that match surface color.

*Culyx.*—Rotate in shape, average of 2 mm in depth and 4 mm in diameter.

*Sepals.*—5, rotate, narrowly ovate in shape, margin entire, an average of 5 mm in length and 2 mm in width, acute apex, cuneate base, both surfaces glossy and densely covered with soft pubescence that matches the surface color, inner and outer surface is 137A in color, texture is thick and succulent.

*Petals.*—An average of 30 per flower, rotate and slightly curved downward, narrowly oblanceolate in shape, surface is smooth and glossy on both surfaces, margin entire, apex acute to rounded, base cuneate, an average of 7 mm in length and 1 mm in width, color; opening and fully open flowers upper surface; base NN155C, mid-section 17A, blending out to the tip 45A, opening and fully open flowers lower surface; base NN155C, blending out to the tip N74A.

*Petaloids.*—An average of 14 per flower, rotate, curved downward over petals, surrounding stamens, lanceolate in shape, moderately to highly glossy on both surfaces, margin entire, apex acute, base cuneate, an average of 4 mm in length and 0.75 mm in width, color upper and lower surface; NN155C, tips 15A.

*Peduncle.*—Average of 3 cm in length and 1 mm in diameter, held in multiple angles, surface is glossy, densely covered with minute pubescence matching surface color, color; 145A.

*Pedicel.*—None.

Reproductive organs:

*Pistils.*—5, an average of 1 mm in length, pistil, style and stigma are not distinguishable, triangular shaped, 138B in color, ovary is 138B in color.

*Stamens.*—Average 40, anthers; dorsifixed and narrowly oblong in shape, an average of 0.5 mm in diameter, 12A in color, filaments are up to 3.5 mm in length 8D in color, pollen is high in quantity and 12A in color.

*Fruit.*—Fruit and seed production was not observed under the conditions tested.

It is claimed:

1. A new and distinct variety of *Delosperma* plant named 'Tangerine Tango' as described and illustrated herein.

* * * * *